United States Patent [19]

Luckey

[11] 4,310,507

[45] Jan. 12, 1982

[54] CONTRAST AGENT FOR RADIOGRAPHY

[75] Inventor: George W. Luckey, Rochester, N.Y.

[73] Assignee: Eastman Kodak Company, Rochester, N.Y.

[21] Appl. No.: 141,030

[22] Filed: Apr. 17, 1980

Related U.S. Application Data

[63] Continuation of Ser. No. 930,289, Aug. 2, 1978, abandoned.

[51] Int. Cl.³ .............................................. A61K 49/04
[52] U.S. Cl. .............................................................. 424/4
[58] Field of Search ............................................ 424/4

[56] References Cited

U.S. PATENT DOCUMENTS 3,832,457  8/1974  Sugimoto et al. .................... 424/4
4,032,471  6/1977  Luckey ......................... 252/301.4 R

OTHER PUBLICATIONS

*Radiographic Contrast Agents,* Miller and Skucas, Univ. Park Press, 1977, pp. 3–5.
*Materials Research Bulletin,* Carnall and Pearlam, 7, pp. 647–654, (1972).
*J. Electrochem. Soc.,* R. C. Ropp, 115, pp. 841–845, (1968).
*Izvestiya Akademii Nauk SSSR,* Tsagareishvili et al., vol. 8, No. 10, pp. 1790–1793, (1972).

*Primary Examiner*—Frederick E. Waddell
*Attorney, Agent, or Firm*—J. Jeffrey Hawley

[57] ABSTRACT

A lanthanide phosphate provides a contrast agent useful in radiographic contrast compositions and surgical elements. Radiographic imaging methods which employ this contrast agent and methods of making lanthanide phosphate-containing radiographic contrast compositions are also disclosed.

11 Claims, No Drawings

CONTRAST AGENT FOR RADIOGRAPHY

This is a continuation of application Ser. No. 930,289, filed Aug. 2, 1978, now abandoned.

FIELD OF THE INVENTION

This invention relates to lanthanide phosphates as radiographic contrast agents and to methods for preparing and using these contrast agents. These agents are particularly useful as contrast agents for use in the X-ray examination of the gastrointestinal tract.

BACKGROUND OF THE INVENTION

Medical radiography is a well-known and extremely valuable tool for the early detection and diagnosis of various disease states of the human body. However, body cavities and the soft tissue of body organs and blood vessels absorb so little X-ray radiation that radiographs of these body portions are difficult to obtain. To overcome this problem, radiologists introduce radiographic contrast agents, sometimes referred to as radiopaques, into such body cavities and tissues. Such contrast agents have been used in the X-ray examination of the human body almost from the days of Roentgen.

The book *Radiographic Contrast Agents*, by R. E. Miller and J. Skucas, University Park Press, 1977, at page 3-5, discloses a variety of materials which have been proposed as contrast agents. These materials include, for example, potassium halides, bismuth subnitrate, bismuth subcarbonate, heavy metals such as cerium, thorium, mercuric sulfide, iron, and zirconium compounds; certain heavy metal chelates; barium titanate; various iodinated organic compounds; and barium sulfate, the latter being the most widely used contrast agent for the gastrointestinal tract.

U.S. Pat. No. 3,832,457 discloses yet another type of radiographic contrast composition which contains finely-divided solid particles of at least one kind of soft magnetic ferrite dispersed in a liquid carrier together with an organic thickening compound, such as starch, and a fine powder of a metallic oxide such as a rare earth oxide, e.g., lanthanum oxide.

Although many different contrast agents have been used in the X-ray examination of the gastrointestinal tract, U.S. Pat. No. 3,368,944 issued Feb. 13, 1968 discloses that the agents thus far employed are far from perfect and often cause undesired effects. Toxicity, of course, is a primary concern because many of the elemental metals present in prior art contrast agents are clearly highly toxic materials. For example, the barium ion is a highly toxic material. Thus, a barium sulfate contrast agent, must be highly purified to eliminate any soluble barium ions.

Other undesired effects also exist. For example, the constipating tendency of barium sulfate is well-known among radiologists, and even small amounts of intravenous barium sulfate act as a purgative. See *Radiographic Contrast Agents*, supra, at page 135. In addition, barium sulfate is well-known as a strong adsorber of all sorts of materials, including a variety of cations, anions, various additives in which the barium sulfate may have been processed, and the like. Because of these strong adsorption properties, barium sulfate contrast agents are easily contaminated. Thus, radiologists must be extremely careful in the selection and use of barium sulfate-containing contrast agents.

Based on the foregoing, the need for the development and use of new contrast agents is readily apparent.

SUMMARY OF THE INVENTION

In accord with the present invention there is provided a radiographic contrast composition and a surgical element comprising as a contrast agent a radiographically effective amount of a lanthanide phosphate and a carrier for this contrast agent. Lanthanide phosphates are the phosphates of heavy metal elements selected from the lanthanide series, i.e., the elements from atomic number 57 through 71 of the Periodic Table of the Elements. This includes lanthanum, cerium, praseodymium, neodymium, promethium, samarium, europium, gadolinium, terbium, dysprosium, holmium, erbium, thulium, ytterbium and lutetium.

Particularly useful lanthanide phosphates employed in the invention are lanthanum phosphate, and mixed lanthanide phosphates wherein a portion of the mixed lanthanide is lanthanum, such as lanthanum terbium phosphate.

The radiographic contrast composition of the invention can be either in dry or liquid state, depending upon the carrier for the lanthanide phosphate contrast agent. For example, in the dry state the lanthanide phosphate can be compounded with any of a variety of suitable binders and prepared, for instance, in tablet form. In liquid state, which represents a highly preferred embodiment, the radiographic contrast composition comprises a stable dispersion of finely-divided lanthanide phosphate particles as contrast agent in an aqueous liquid carrier, the particles having a particle size of from about 0.1 to 10 microns and the dispersion having a density within the range of from about 1.4 to 1.8 g/ml.

In a further embodiment, a surgical element is provided which comprises a surgical article as a carrier, e.g., a surgical instrument, dressing, suture, or implant, and a radiographically effective amount of a lanthanide phosphate as a contrast agent.

The present invention also provides a method of forming a radiographic image of a body portion, for example, a body cavity or body organ, of a test subject which comprises:

(a) introducing into the body portion as a contrast agent a radiographically effective amount of a lanthanide phosphate, (b) exposing the body portion containing the contrast agent to X-rays to form an X-ray image pattern corresponding to the presence of the contrast agent, and (c) visualizing the image pattern.

A further embodiment of the invention provides a method of making a radiographic contrast composition containing a lanthanide phosphate contrast agent.

DESCRIPTION OF THE PREFERRED EMBODIMENTS

The lanthanide phosphates employed in the invention effectively absorb X-rays and are highly water-insoluble. The solubility product, for example, of lanthanum phosphate has been calculated to be $3.75 \times 10^{-23}$ in water at a temperature of 25° C. See I. V. Tananaev et al, *Russian Journal of Inorganic Chemistry*, 8, No. 5, page 555-558 (1963).

A preferred embodiment of the invention provides a radiographic contrast composition comprising a lanthanide phosphate-containing aqueous dispersion having a density within the range of from about 1.4 to about 1.8 g/ml. Typically, these dispersions are quite stable, exhibiting little or no gelling when allowed to stand under ambient temperature and atmospheric conditions for periods of times in excess of about one month. The particle sizes of the lanthanide phosphate particles contained in these aqueous dispersions are typically within the size range of from about 0.1 to 10 microns, preferably from about 0.2 to 2 microns, to minimize undesired settling out of the lanthanide phosphate particles and to optimize the density of the dispersion to a value within the preferred density range of from about 1.6 to about 1.8 grams per milliliter.

In accord with the invention, the preferred method of preparing the above-described lanthanide phosphate-containing dispersions comprises (a) heating an aqueous phosphoric acid solution having a concentration within the range of from about 3 M to 0.1 M to a temperature in excess of about 80° C. and less than the boiling point of the acid, (b) slowly admixing finely-divided crystals consisting essentially of a lanthanide oxide into the heated acid to form a heated mixture containing said crystals, the amount of said crystals regulated to provide a molar excess of phosphoric acid in said heated mixture, whereby the lanthanide oxide reacts with phosphoric acid in said mixture to provide finely-divided particles of a lanthanide phosphate, and (c) neutralizing said heated mixture by addition of base to provide a pH of about 7.0.

In carrying out the method of preparing the lanthanide phosphate-containing dispersion, useful results can be obtained using various reagent grade commercial preparations of the selected lanthanide oxide employed in step (b) of the method of the invention. However, best results have thus far been obtained wherein the lanthanide oxide employed in step (b) of the method was a mixed lanthanide oxide prepared in the manner described, for example, in U.S. Pat. No. 4,032,471 issued June 28, 1977, or in the article by E. Carnall and O. Pearlman, *Materials Research Bulletin* 7 647–654 (1972). A preferred mixed lanthanide oxide is lanthanum terbium oxide containing about 0.1 to 2 percent terbium.

The phosphoric acid employed in step (a) of the method of making the lanthanide phosphate can be concentrated phosphoric acid or, as is preferred, an aqueous solution of phosphoric acid having a concentration within the range of from about 3 M to 0.1 M. When an aqueous solution of phosphoric acid is employed, the water content of the lanthanide phosphate dispersion may have to be adjusted following step (c) to obtain a suspension having the desired density in excess of about 1.40 grams per milliliter.

By preparing a lanthanide phosphate dispersion as described herein, one produces a dispersion of high density and thus particularly effective for use as a radiographic contrast composition. The density of these dispersions is, in large part, regulated by the particle size of the lanthanide phosphate in the dispersion. The method provides finely-divided particles of a lanthanide phosphate having a particle size which produces high density and stable dispersions, i.e., the particles do not readily settle out of suspension. A useful particle size for the lanthanide phosphate particles employed in the invention is within the range of from about 0.1 to 10 microns, with a preferred particle size being from about 0.2 to 2 microns to provide stable, high density dispersions.

If the lanthanide phosphate contrast agent is to be stored prior to use, a preferred method for preparing a lanthanide phosphate dispersion of suitable particle size can include a final drying step to remove all water from the dispersion. A dry, particulate lanthanum phosphate powder remains. The powder may be stored as is, or the powder can be combined with an appropriate dry binder, as well as any other optional additives described hereinafter, and formed into dry tablets. The powder or tablets can readily be redispersed in an aqueous liquid carrier immediately prior to use to provide an aqueous dispersion of appropriate density.

The carrier employed in the radiographic compositions of the invention can be either wet or dry. For example, in accord with a preferred embodiment the carrier is an aqueous liquid media. This is generally the form of the carrier at the time the lanthanide phosphate is introduced into the body of the test subject. In such case, the carrier is typically an aqueous liquid, including an optional buffer and any other additives as described hereinafter. Alternatively, where the contrast agent of the invention is prepared or used in dry tablet form, the carrier for the agent may be a suitable binder such as a natural or synthetic polymer, for example, dextrin, starch, gelatin, etc.

In still other embodiments, an element comprising the lanthanide phosphate contrast agent described herein and a suitable dry carrier are provided. For example, the element can be a surgical element which contains the lanthanide phosphate contrast agent and a carrier such as a surgical instrument, dressing, suture, implant, and the like. In such case, the presence of the contrast agent in or on the carrier enables one to readily identify and locate the position of the element within a body portion of a patient.

The lanthanide phosphate contrast agents of the invention can, of course, be admixed with one or more of various conventional additives used to control and enhance the properties of radiographic contrast agents. For example, buffers, viscosity regulating agents, suspending agents, peptizing agents, mixing agents, and the like can be added. A partial listing of certain specific additives includes sugars, gelatin, sodium alginate, agar, gum arabic, albumin, dextrin, pectin, and sodium carboxymethyl cellulose. It will be understood that such additives as well as various other grinding agents, surface active agents, sweetening agents, flavoring agents, drugs, preservatives and the like can be incorporated in the radiographic contrast compositions and elements of the invention. Such additives are conventional in the art and further detail concerning the use and type of these additives may be found by reference to Miller and Skucas, *Radiographic Contrast Agents*, supra, pages 37–141.

The method of forming a radiographic image by use of the radiographic contrast compositions of the invention can be carried out in accord with established radiographic techniques and procedures. Thus, the method includes the steps of introducing the contrast agent into a body portion of the test subject, exposing that portion of the test subject containing the contrast agent to X-rays to produce an X-ray image pattern corresponding to the presence of the contrast agent, and visualizing this image pattern, the specific improvement afforded by the image-forming method of the invention being the introduction of a lanthanide phosphate as all or part of the contrast agent.

The introduction of the lanthanide phosphate contrast agent into the body of the test subject can be accomplished orally, by use of an enema, or other known techniques. Typically, the lanthanide phosphate contrast agents are injected in the form of an aqueous suspension; however they could also be administered in dry tablet form or in admixture with a suitable foodstuff. The dosage level, as will be readily appreciated, is in large part determined by the organ, body cavity, physical size of the test subject, as well as the size and type of radiograph desired. For example, when the radiographic contrast compositions are employed as gastrointestinal contrast agents in accord with a preferred embodiment of the invention, a typical adult dosage would be in the range of from about 10 to 400 g of lanthanide phosphate.

Visualization of the X-ray image can be carried out by well-known techniques including the use of a conventional X-ray sensitive phosphor screen—silver halide photographic film combination; various electrophotographic techniques such as xeroradiography; and other radiographic visualization techniques such as ionography.

The following example is presented to further illustrate the invention.

EXAMPLE

A mixed lanthanum terbium oxide was prepared having a mole fraction of terbium oxide in the mixed oxide of 0.0053. The mixed lanthanum terbium oxide was prepared as described in paragraphs A–C below.

A. About 176 moles of oxalic acid was dissolved in sufficient distilled water to make 180 liters of solution which was filtered through a Millipore ® Filter having a pore size of 0.47 micron.

B. A second solution was prepared by dissolving 58.3 moles lanthanum oxide and 0.311 mole terbium oxide in 28.5 liters of 37.5 percent hydrochloric acid and sufficient distilled water to make 120 liters. This solution was also filtered with the Millipore ® Filter.

C. Then 363 liters of distilled water were mixed with 41.7 liters of the lanthanum solution in a 1360 liter reaction vessel and stirred vigorously while the oxalate ion solution and distilled water were added at 1.5 and 2.7 liters per minute, respectively, and simultaneously the remaining lanthanum-terbium solution was added at a rate of 0.65 liter per minute. The temperature of the reaction was 90° C. throughout. When the addition was complete, the precipitate was ripened for 15 minutes at 90° C., then washed with distilled water until the washings were neutral. The precipitate was then dried and fired for 2 hours in air at 900° C. This procedure produced a material identified as $La_2O_3:Tb(0.005)$.

D. The lanthanum phosphate was prepared by mixing 300 ml of distilled water and 114 grams or 70 ml of Reagent Grade phosphoric acid (86 percent $H_3PO_4$ by weight), heating the solution to 90° C., then adding 163 grams of the $La_2O_3:Tb(0.005)$ made as described in preceding paragraphs A–C. The time of addition was 30 minutes. Then 8 grams of sodium hydroxide and water to make 20 ml was added to the mixture to neutralize the solution and increase the pH to 7. The suspension was stirred at 90° C. for 20 minutes. After settling, sufficient water could be removed to make the density 1.67 grams/ml, or about 83 percent w/v. A sample of the precipitate was dried and X-ray diffraction showed that it consisted of small crystals of lanthanum phosphate doped with terbium. The grain size of the crystals was within the preferred size range of from about 0.2 to 2 microns.

E. The aqueous suspension of paragraph D was then fed to a rat (0.35 ml) and a rabbit (7.8 ml) by stomach tube. These animals and unfed control animals were then radiographed with a variety of screen-film-process combinations. The radiographs were made with 70 kVp X-rays filtered by ½ mm copper and 1 mm aluminum, with the animal at a distance of 150 cm from the X-ray source. The current was 100 mA and the times of 23.6 cm exposure are given in Table I. The films were all processed in a Kodak RP X-OMAT Processor with Kodak MX-810 Developer in the usual cycle.

TABLE I

| Radiographic Exposure Times | | |
|---|---|---|
| Screen-Film Combination | Time, Rat (in seconds) | Time, Rabbit (in seconds) |
| KODAK X-OMATIC Regular Screens KODAK X-OMAT RP Film, 4517 | 0.1 | 3/20 |
| KODAK LANEX Regular Screens KODAK X-OMAT G Film, 4506 | 1/30 | |
| GE Blue MAX 2 Screens KODAK X-OMAT RP Film, 4517 | 1/30 | |
| DuPont Par Speed Screens KODAK X-OMAT RP Film, 4517 | 3/20 | |

Because the lanthanide phosphate materials employed as a contrast agent in the present invention are clearly different from contrast agents now employed in the art, e.g., barium sulfate, these lanthanide phosphate contrast agents offer the possibility of quite different surface characteristics when used as contrast agents in the body. For example, the lanthanide phosphates may coat the surfaces in the gastrointestinal tract more effectively than currently employed barium sulfate contrast agents.

The contrast agent was clearly visible in all of the radiographs. The filled anatomical structures were not visible in the control animals. The rabbit which was given the $LaPO_4$ dispersion behaved normally for four days after administration of the dose. The stools from this rabbit were larger than usual, but no ill effects were caused. No harmful effect was observed in the rat, although this animal was sacrificed shortly after the dose was administered.

The invention has been described in detail with particular reference to certain preferred embodiments thereof, but it will be understood that variations and modifications can be effected within the spirit and scope of the invention.

I claim:

1. A radiographic contrast composition comprising a radiographically effective amount of a lanthanide phosphate as a contrast agent and a carrier for said agent, wherein said carrier is a natural or synthetic polymer binder and said composition is in dry tablet form.

2. A radiographic contrast composition comprising an aqueous dispersion containing a radiographically effective amount of finely-divided lanthanide phosphate particles, said particles having a size within the range of from about 0.1 to 10 microns and said dispersion having a density in excess of 1.4 g/ml.

3. A radiographic contrast composition as defined in claim 2 wherein said lanthanide phosphate is lanthanum phosphate, or a mixed lanthanide phosphate containing lanthanum as a portion of said mixed lanthanide.

4. A radiographic contrast composition as defined in claim 2 wherein said particles have a size within the range of from about 0.2 to 2 microns and said dispersion has a density within the range of from about 1.6 to 1.8 g/ml.

5. A radiographic contrast composition as defined in claim 2 wherein said lanthanide phosphate is a terbium-doped lanthanum phosphate.

6. A method of making an aqueous radiographic contrast composition comprising
  (a) heating an aqueous phosphoric acid solution having a concentration within the range of about 3 M to 0.1 M to a temperature in excess of 80° C. and less than the boiling point of said acid,
  (b) slowly admixing finely-divided crystals consisting essentially of a lanthanide oxide into the heated acid to form a heated mixture containing said crystals, the amount of said crystals regulated to provide a molar excess of phosphoric acid in said heated mixture, whereby the lanthanide oxide reacts with phosphoric acid in said mixture to provide finely-divided particles of a lanthanide phosphate, and
  (c) neutralizing said heated mixture by addition of base.

7. A method of making a radiographic contrast composition as defined in claim 6 wherein following step (c) the amount of water contained in said composition is adjusted to provide a composition having a density in excess of 1.4 g/ml.

8. A method of making a radiographic contrast composition as defined in claim 6 wherein said lanthanide oxide is lanthanum oxide or a mixed lanthanide oxide containing lanthanum as a portion of said mixed lanthanide.

9. A method of forming a radiographic image of a body portion of a test subject which comprises:
  (a) introducing a radiographically effective amount of a lanthanide phosphate as a contrast agent into said body portion;
  (b) exposing said body portion containing said contrast agent to X-rays to form an X-ray image pattern corresponding to the presence of said contrast agent, and
  (c) visualizing said image pattern.

10. A method of forming a radiographic image as defined in claim 9 wherein said lanthanide phosphate is lanthanum phosphate, or a mixed lanthanide phosphate containing lanthanum as a portion of said mixed lanthanide.

11. A method of forming a radiographic image as defined in claim 9 wherein said contrast agent is introduced into said body portion as finely-divided particles dispersed in an aqueous carrier liquid.

* * * * *